US012715828B2

(12) United States Patent
Saijo et al.

(10) Patent No.: US 12,715,828 B2
(45) Date of Patent: Aug. 25, 2026

(54) TRICYCLODECANE DIMETHANOL COMPOSITION, ULTRAVIOLET CURABLE COMPOSITION, POLYMER COMPOSITION, AND METHOD FOR PRODUCING TRICYCLODECANE DIMETHANOL COMPOSITION

(71) Applicant: Mitsubishi Chemical Corporation, Tokyo (JP)

(72) Inventors: Hiroki Saijo, Chiyoda-ku (JP); Naoto Tashima, Chiyoda-ku (JP); Yoshiyuki Tanaka, Chiyoda-ku (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 18/887,917

(22) Filed: Sep. 17, 2024

(65) Prior Publication Data

US 2025/0026703 A1 Jan. 23, 2025

Related U.S. Application Data

(63) Continuation of application No. PCT/JP2023/008851, filed on Mar. 8, 2023.

(30) Foreign Application Priority Data

Mar. 17, 2022 (JP) ................................ 2022-042785

(51) Int. Cl.

| | |
|---|---|
| ***C07C 31/27*** | (2006.01) |
| ***C09D 4/00*** | (2006.01) |
| ***C09D 5/16*** | (2006.01) |
| ***C09D 11/101*** | (2014.01) |
| ***C09D 11/104*** | (2014.01) |
| ***C09D 11/107*** | (2014.01) |
| ***C09D 11/30*** | (2014.01) |

(Continued)

(52) U.S. Cl.

CPC .............. *C07C 31/278* (2013.01); *C09D 4/00* (2013.01); *C09D 5/1662* (2013.01);

(Continued)

(58) Field of Classification Search

CPC ..... C07C 31/278; C07C 2603/66; C09D 4/00; C09D 5/1662; C09D 11/101;

(Continued)

(56) References Cited

U.S. PATENT DOCUMENTS

| | | | |
|---|---|---|---|
| 10,538,472 | B1 | 1/2020 | Chou et al. |
| 10,767,004 | B1 | 9/2020 | Chiu et al. |

(Continued)

FOREIGN PATENT DOCUMENTS

| | | |
|---|---|---|
| JP | 2020-132624 A | 8/2020 |
| JP | 2021-520401 A | 8/2021 |

(Continued)

OTHER PUBLICATIONS

Kolb, B., Ettre, L. S.(2006). Static Headspace-Gas Chromatography: Theory and Practice. Germany Wiley. p. 22 (Year: 2006).*

(Continued)

*Primary Examiner* — Mark F. Huff
*Assistant Examiner* — Richard David Champion
(74) *Attorney, Agent, or Firm* — Oblon, McClelland, Maier & Neustadt, L.L.P.

(57) ABSTRACT

A tricyclodecane dimethanol composition comprising tricyclodecane dimethanols, wherein the tricyclodecane dimethanols comprise a chiral compound A, one of whose enantiomers represented by the following formula (I), a chiral compound B, one of whose enantiomers represented by the following formula (II), and a chiral compound C, one of whose enantiomers represented by the following formula (III), and a peak area Xc of the chiral compound C in a gas chromatogram and a total peak areas Xt of tricyclodecane dimethanols in a gas chromatogram, which are detected by a gas chromatography, satisfy Xc/Xt≥0.35.

20 Claims, 1 Drawing Sheet

(51) Int. Cl.
*C09D 135/02* (2006.01)
*C09D 163/00* (2006.01)
*C09D 167/02* (2006.01)
*C09D 169/00* (2006.01)
*C09D 175/04* (2006.01)
*G03F 7/027* (2006.01)

(52) U.S. Cl.
CPC .......... *C09D 11/101* (2013.01); *C09D 11/104* (2013.01); *C09D 11/107* (2013.01); *C09D 11/30* (2013.01); *C09D 135/02* (2013.01); *C09D 163/00* (2013.01); *C09D 167/02* (2013.01); *C09D 169/00* (2013.01); *C09D 175/04* (2013.01); *G03F 7/027* (2013.01); *C07C 2603/66* (2017.05)

(58) Field of Classification Search
CPC ..... C09D 11/104; C09D 11/107; C09D 11/30; C09D 135/02; C09D 163/00; C09D 167/02; C09D 169/00; C09D 175/04; G03F 7/027
See application file for complete search history.

(56) References Cited

U.S. PATENT DOCUMENTS

| | | | |
|---|---|---|---|
| 2005/0107644 A1 | 5/2005 | Lappe et al. | |
| 2023/0192579 A1 | 6/2023 | Chae et al. | |
| 2023/0279243 A1 * | 9/2023 | Chae | C07C 29/141 568/818 |

FOREIGN PATENT DOCUMENTS

| | | | | |
|---|---|---|---|---|
| JP | 7513199 | | 7/2024 | |
| KR | 102389695 | B1 | 4/2022 | |
| KR | 2435355 | B1 * | 8/2022 | C09D 7/20 |
| WO | 2009013063 | A1 | 1/2009 | |
| WO | 2009013064 | A2 | 1/2009 | |
| WO | 2009068377 | A1 | 6/2009 | |
| WO | 2022265240 | A1 | 12/2022 | |
| WO | 2023277347 | A1 | 1/2023 | |
| WO | 2023-176641 | A1 | 9/2023 | |

OTHER PUBLICATIONS

International Search Report and Written Opinion issued May 23, 2023 in PCT/JP2023/008851 filed Mar. 8, 2023, 8 pages.

Douglas L. Hunter et al. "Dicyclopentadiene hydroformylation catalyzed by $Rh_xCo_{4-x}(CO)_{12}$ (x =4, 2-0)/tertiary amine catalysts [1]" Applied Catalysis, vol. 19, Issue 2, Dec. 16, 1985, pp. 259-273.

Tooru Kikuchi et al. "Stereostructure and Composition of Products from Hydroformylation of Dicyclopentadiene using Carbon Dioxide as a Reactant" Hitachi Chemical technical Report, No. 51, 2008, pp. 7-12.

Extended European Search Report issued Oct. 1, 2025 in a corresponding European Application No. 2377059, 7 pages.

Fuchs et al., "Synthesis of Industrial Primary Diamines via Intermediate Diols—Combining Hydroformylation, Hydrogenation and Amination", ChemCatChem, Jan. 1, 2018, 23 pages, XP093316454.

* cited by examiner

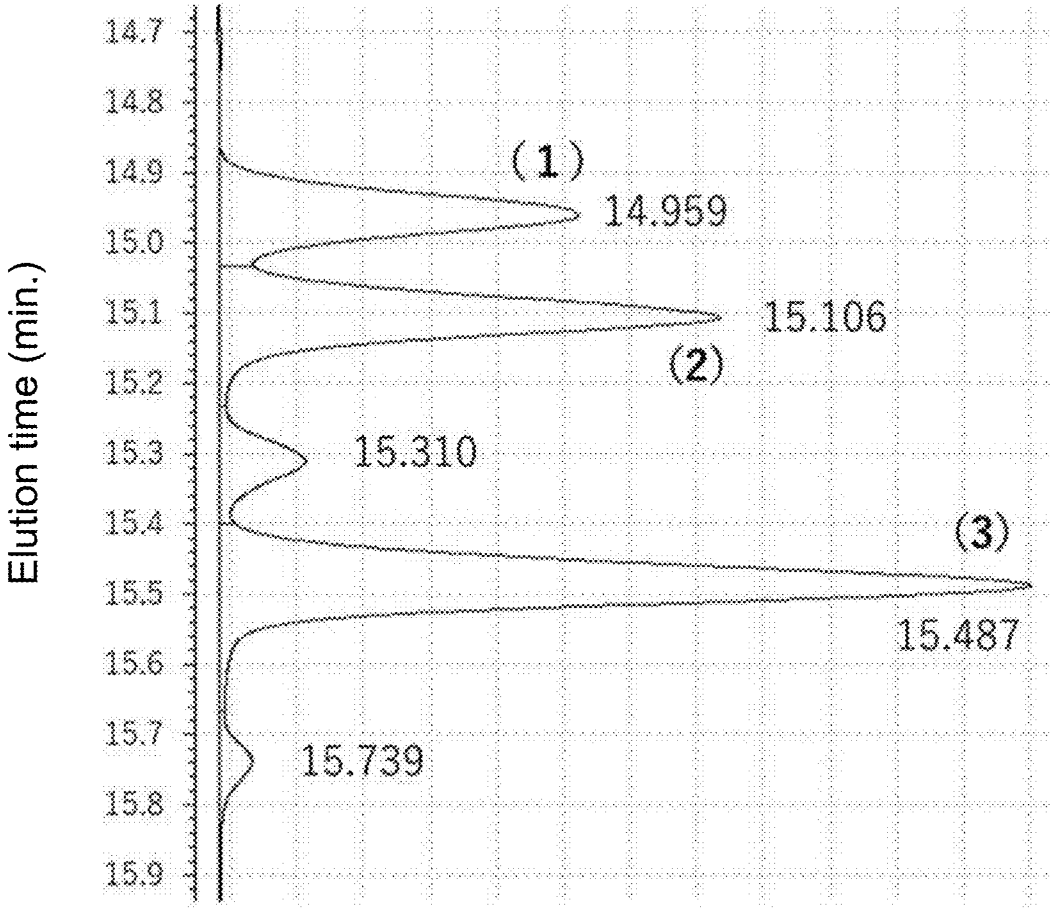
Elution time (min.)
14.7
14.8
14.9
15.0
15.1
15.2
15.3
15.4
15.5
15.6
15.7
15.8
15.9
(1)
14.959
15.106
(2)
15.310
(3)
15.487
15.739

TRICYCLODECANE DIMETHANOL COMPOSITION, ULTRAVIOLET CURABLE COMPOSITION, POLYMER COMPOSITION, AND METHOD FOR PRODUCING TRICYCLODECANE DIMETHANOL COMPOSITION

CROSS-REFERENCE TO RELATED APPLICATIONS

This is a bypass continuation of International Patent Application No. PCT/JP2023/008851, filed on Mar. 8, 2023, which claims priority to Japanese Patent Application No. 2022-042785, filed on Mar. 17, 2022. The contents of these applications are hereby incorporated by reference in their entireties.

TECHNICAL FIELD

The present invention relates to a tricyclodecane dimethanol composition, ultraviolet curable composition, polymer composition, and method for producing tricyclodecane dimethanol composition.

BACKGROUND ART

In the fields of molding materials, electronic materials, and display device components, materials having alicyclic molecular structures are used from the viewpoints of transparency, heat resistance, and low water absorption.

Tricyclodecane dimethanol (hereinafter abbreviated as "TCDDM") is a dihydric alcohol having an alicyclic structure. TCDDM is produced by hydroformylating dicyclopentadiene with carbon monoxide and hydrogen in the presence of a catalyst to produce an aldehyde, and then reducing the obtained aldehyde with hydrogen. (Patent Literature 1, Patent Literature 2)

TCDDM has been used as a synthetic raw material for molding materials such as polyester, polycarbonate, and the like. Polymers containing TCDDM as a constituent are known to exhibit excellent performance in terms of hardness, transparency, heat resistance, and low water absorption due to their alicyclic structure. For this reason, polymers containing TCDDM as a constituent are used in the fields of molding materials, electronic materials, and display device components.

TCDDM derivatives such as diacrylate derivatives, dimethacrylate derivatives, and urethane acrylates, which are synthesized using TCDDM as a raw material, are used as ultraviolet curable compositions.

Cured products made by ultraviolet curable compositions containing TCDDM as a structural component have characteristics such as high surface hardness, high glass transition temperature, excellent thermal decomposition resistance, and excellent development resistance. For this reason, cured products made by ultraviolet curable compositions containing TCDDM as a structural component are used in electronic materials such as hard coats, antifouling coats, resists, and the like, and display device components.

In the method of producing TCDDM by hydroformylating dicyclopentadiene, the reactivity of the double bond of the norbornene ring of dicyclopentadiene is higher than that of the double bond of the five-membered ring. Therefore, after the first formyl group is added to the norbornene ring, the second formyl group is added to the double bond of the five-membered ring. (Non-Patent Literature 1) As a result, it is known that the TCDDM obtained by this reaction is a mixture of TCDDM (hereinafter referred to as "TCDDM composition") mainly composed of three types of isomers having different bonding positions of a hydroxymethyl group in the five-membered ring. (Non-Patent Literature 2)

CITATION LIST

Patent Literature

Patent Literature 1: JP 2020-132624 A
Patent Literature 2: JP 2021-520401 A

Non-Patent Literature

Non-Patent Literature 1: Hitachi Chemical Technical Report, No. 51 (2008-7), pp. 7-12
Non-Patent Literature 2: Applied Catalyst, Vol. 19, pp. 259-273 (1985)

SUMMARY OF INVENTION

Technical Problem

The TCDDM compositions described in Patent Literatures 1 and 2 are difficult to handle because they tend to become stringy during handling such as blending operations, and the like.

For this reason, when handling conventional TCDDM compositions as raw materials for producing polymers or ultraviolet curable compositions, there has been a demand for improved handling properties by reducing stringiness so that they are free from adhering to containers or equipment and reducing productivity.

In fields where an ultraviolet curable composition synthesized using TCDDM as a raw material is used, a method of applying an ultraviolet curable composition to a substrate using a screen printing method or a flex printing method and curing the composition is used for applications such as resists. In this case, the ultraviolet curable composition is required to have a high viscosity from the viewpoint of being able to apply thinly and uniformly, or thickly, and being able to print fine patterns on a substrate with high precision.

For applications such as hard coats, antifouling coats, inkjet printings, and the like, a coater method, a spray method, or a dispenser method is used to apply an ultraviolet curable composition to a substrate and cure it. Even in this case, the ultraviolet curable composition is required to have a high viscosity from the viewpoint of accurately discharging a fixed amount of the ultraviolet curable composition.

However, the viscosity of the ultraviolet curable compositions synthesized using conventional TCDDM as a raw material is significantly reduced as a result of converting the alcohol moiety of TCDDM to an ester bond or the like. When a viscosity improver is added to increase the viscosity, the performance originally required of the ultraviolet curable composition is impaired.

An object of the present invention is to provide a TCDDM composition having reduced stringiness and excellent handling properties.

An object of the present invention is also to provide a TCDDM composition from which a high viscosity ultraviolet curable composition can be obtained.

Solution to Problem

The present inventors have found that it is effective to appropriately control an isomer ratio in a TCDDM mixture mainly composed of three isomers having different bonding positions of the hydroxymethyl group. More specifically, the inventors have found that one of the three isomers has an extremely highly crystalline structure, and that by producing the composition so that the ratio of this component is equal to or more than a predetermined value, the crystallinity of the TCDDM composition can be adjusted, and a TCDDM composition that is less likely to become stringy and has excellent handling properties can be obtained. Furthermore, the inventors have found that by using a TCDDM composition containing a large amount of highly crystalline structures as a raw material, it is possible to improve the orientation of the molecular structure, and obtain a high viscosity ultraviolet curable composition can be obtained.

The present invention is summarized as follows.

[1] A tricyclodecane dimethanol composition comprising tricyclodecane dimethanols, wherein the tricyclodecane dimethanols comprise a chiral compound A, one of whose enantiomers represented by the following formula (I), a chiral compound B, one of whose enantiomers represented by the following formula (II), and a chiral compound C, one of whose enantiomers represented by the following formula (III), and a peak area Xc of the chiral compound C in a gas chromatogram and a total peak areas Xt of tricyclodecane dimethanols in a gas chromatogram, which are detected by a gas chromatography, satisfy Xc/Xt≥0.35.

[Chem. 1]

(I)

(II)

(III)

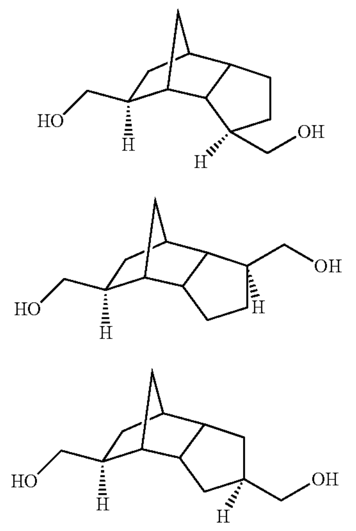

[2] The tricyclodecane dimethanol composition according to [1], wherein a peak area Xb of the chiral compound B in a gas chromatogram and the Xc, which are detected by a gas chromatography, satisfy Xc/Xb≥1.00.

[3] The tricyclodecane dimethanol composition according to [1] or [2], wherein a peak area Xa of the chiral compound A in a gas chromatogram, a peak area Xb of the chiral compound B in a gas chromatogram, and the Xc, which are detected by a gas chromatography, satisfy Xc/(Xa+Xb) ≥0.60.

[4] The tricyclodecane dimethanol composition according to any one of [1] to [3], wherein a peak area Xa of the chiral compound A in a gas chromatogram and the Xt, which are detected by a gas chromatography, satisfy Xa/Xt≤0.27.

[5] The tricyclodecane dimethanol composition according to any one of [1] to [4], wherein a peak area Xb of the chiral compound B in a gas chromatogram and the Xt, which are detected by a gas chromatography, satisfy Xb/Xt≤0.32.

[6] An ultraviolet curable composition derived from the tricyclodecane dimethanol composition according to any one of [1] to [5].

[7] The ultraviolet curable composition according to [6], wherein the composition is used for any one of hard coating materials, antifouling coating materials, resist materials, inkjet inks, and materials for 3D printers.

[8] A polymer composition derived from the tricyclodecane dimethanol composition according to any one of [1] to [5], or the ultraviolet curable composition according to [6] or [7].

[9] The polymer composition according to [8], wherein the composition is at least one selected from the group consisting of polyester resins, epoxy resins, acrylate resins, polycarbonate resins, and polyurethane resins.

[10] A method for producing the tricyclodecane dimethanol composition according to any one of [1] to [5], comprising a step of hydroformylating dicyclopentadiene to obtain tricyclodecane dicarbaldehydes, a step of obtaining a crude reaction solution containing tricyclodecane dimethanol by a reduction reaction of the tricyclodecane dicarbaldehyde, and a step of distilling and purifying the crude reaction solution to obtain a tricyclodecane dimethanol composition.

Advantageous Effects of Invention

According to the present invention, it is possible to provide a TCDDM composition that is highly crystalline and has excellent handling properties. More specifically, the TCDDM composition of the present invention has excellent crystallinity by appropriately selecting the isomer ratio. As a result, stringiness during handling of the TCDDM composition can be reduced, and production efficiency can be improved.

Furthermore, an ultraviolet curable composition synthesized using the TCDDM composition of the present invention as a raw material has excellent coating stability because it can be controlled to a high viscosity without impairing the performance originally required of the ultraviolet curable composition.

BRIEF DESCRIPTION OF DRAWINGS

FIG. 1 shows a gas chromatogram of the TCDDM composition obtained in Example 3.

DESCRIPTION OF EMBODIMENTS

The present invention will be described in detail below. The present invention is not limited to the following description as long as it does not exceed the gist of the invention, and can be carried out with any modification within the scope of the gist of the present invention.

Unless otherwise specified, in this specification, a numerical range expressed using "to" means a range including the numerical values written before and after "to" as the lower and upper limits. "A to B" means A or more and B or less.

<TCDDM Composition>

The TCDDM composition of the present invention is a composition containing tricyclodecane dimethanols.

The tricyclodecane dimethanols are a mixture of a chiral compound A, one of whose enantiomers represented by the following formula (I), a chiral compound B, one of whose enantiomers represented by the following formula (II), and a chiral compound C, one of whose enantiomers represented by the following formula (III).

The chiral compound A, the chiral compound B, and the chiral compound C have one hydroxymethyl group ($CH_2OH$ group) in the 6-membered ring moiety of the norbornane ring and another one hydroxymethyl group in the 5-membered ring moiety, as shown in the following general formulas (I) to (III).

[Chem. 2]

(I)

(II)

(III)

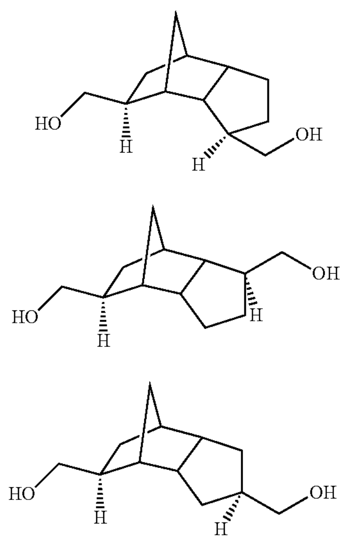

More specifically, the tricyclodecane dimethanols of the present invention include a chiral compound A consisting of a compound represented by the following formula (I) and a compound represented by the following formula (IA) which is an enantiomer of this compound, a chiral compound B consisting of a compound represented by the following formula (II) and a compound represented by the following formula (IIA) which is an enantiomer of this compound, and a chiral compound C consisting of a compound represented by the following formula (III) and a compound represented by the following formula (IIIA) which is an enantiomer of this compound.

[Chem. 3]

(I)

(IA)

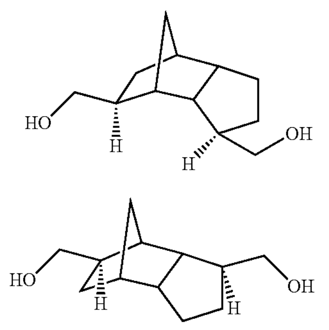

-continued (II)

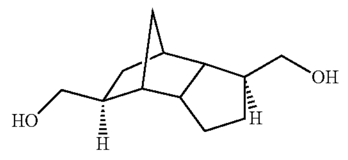

(IIA)

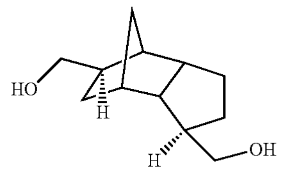

(III)

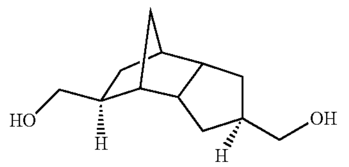

(IIIA)

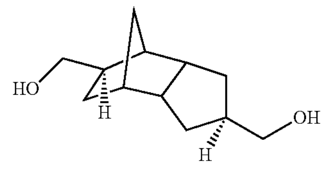

Thus, in the chiral compound A, the chiral compound B, and the chiral compound C of the present invention, R-form and S-form exist as enantiomers (also called optical isomers), but the difference between them is not particularly important, and both are included.

Furthermore, the chiral compound A, the chiral compound B, and the chiral compound C in the present invention have stereoisomers depending on whether the two hydroxymethyl groups are bonded to the same side as the bridgehead position of the norbornane ring or to the opposite side. However, as shown in the formulas (I) to (III) or the formulas (IA) to (IIIA), the hydroxymethyl groups are bonded to the same side as the bridgehead position of the norbornane ring. Furthermore, although the tricyclodecane skeleton has both an endo form and an exo form, the chiral compound A, the chiral compound B, and the chiral compound C in the present invention have only the endo form.

Compounds in which the hydroxymethyl groups are bonded to the opposite side of the bridgehead position and compounds in which the tricyclodecane skeleton is an exo form may or may not be included in the tricyclodecane dimethanols as other components. The "total peak areas Xt of tricyclodecane dimethanols in a gas chromatograms" includes the peak areas of these compounds.

Hereinafter, "chiral compound A", "chiral compound B", and "chiral compound C" may be referred to simply as "compound A", "compound B", and "compound C", respectively.

In the TCDDM composition of the present invention, the lower limit of Xc/Xt calculated from the peak area Xc of the chiral compound C in a gas chromatogram and the total peak areas Xt of tricyclodecane dimethanols in a gas chromatogram, which are detected by a gas chromatography, is $Xc/Xt \geq 0.35$, from the viewpoint of the handling properties of the composition. This ratio is preferably $Xc/Xt \geq 0.38$, and more preferably $Xc/Xt \geq 0.42$. On the other hand, the upper limit of Xc/X is not particularly limited, but from the viewpoint of maintaining good handling properties of the composition, the ratio is usually preferably $Xc/Xt \leq 0.55$, and more preferably $Xc/Xt \leq 0.50$.

The means for controlling the above mentioned value of Xc/Xt is not particularly limited, and a person skilled in the art can control it by optimizing the producing conditions appropriately according to known techniques. For example, the above mentioned value of Xc/Xt can be controlled by optimizing the reaction conditions of hydroformylation, the distillation conditions when distilling and purifying the obtained TCDDM composition, and the like.

In the TCDDM composition of the present invention, the lower limit of Xc/Xb calculated from the peak area Xb of the compound B in a gas chromatogram detected by a gas chromatography and the above Xc is preferably $Xc/Xb \geq 1.00$, more preferably $Xc/Xb \geq 1.25$, and even more preferably $Xc/Xb \geq 1.50$, from the viewpoint of the handling properties of the composition. On the other hand, the upper limit of Xc/Xb is not particularly limited, but from the viewpoint of maintaining good handling properties of the composition, the ratio is usually preferably $Xc/Xb \leq 3.0$, and more preferably $Xc/Xb \leq 2.0$.

The means for controlling the above mentioned value of Xc/Xb is not particularly limited, and a person skilled in the art can control it by optimizing the producing conditions appropriately according to known techniques. For example, the above mentioned value of Xc/Xb can be controlled by optimizing the reaction conditions of hydroformylation, the distillation conditions when distilling and purifying the obtained TCDDM composition, and the like.

In the TCDDM composition of the present invention, the lower limit of Xc/(Xa+Xb) calculated from the peak area Xa of the compound A in a gas chromatogram detected by a gas chromatography, the above mentioned Xb, and the above mentioned Xc, is preferably $Xc/(Xa+Xb) \geq 0.60$, more preferably $Xc/(Xa+Xb) \geq 0.70$, and even more preferably $Xc/(Xa+Xb) \geq 0.80$, from the viewpoint of the handling properties of the composition. On the other hand, the upper limit of Xc/(Xa+Xb) is not particularly limited, but from the viewpoint of maintaining good handling properties of the composition, the ratio is usually preferably $Xc/(Xa+Xb) \leq 1.10$, and more preferably $Xc/(Xa+Xb) \leq 1.00$.

The means for controlling the above mentioned value of Xc/(Xa+Xb) is not particularly limited, and a person skilled in the art can control it by optimizing the producing conditions appropriately according to known techniques.

For example, the above mentioned value of Xc/(Xa+Xb) can be controlled by optimizing the reaction conditions of hydroformylation, the distillation conditions when distilling and purifying the obtained TCDDM composition, and the like.

In the TCDDM composition of the present invention, the upper limit of Xa/Xt calculated from the above mentioned Xa and the above mentioned Xt is preferably $Xa/Xt \leq 0.27$, and more preferably $Xa/Xt \leq 0.23$, from the viewpoint of the handling properties of the composition. On the other hand, the lower limit of Xa/Xt is not particularly limited, but from the viewpoint of maintaining good handling properties of the composition, the ratio is usually preferably $Xa/Xt \geq 0.18$, and more preferably $Xa/Xt \geq 0.20$.

The means for controlling the above mentioned value of Xa/Xt is not particularly limited, and a person skilled in the art can control it by optimizing the producing conditions appropriately according to known techniques. For example, the above mentioned value of Xa/Xt can be controlled by optimizing the reaction conditions of hydroformylation, the distillation conditions when distilling and purifying the obtained TCDDM composition, and the like.

In the TCDDM composition of the present invention, the upper limit of Xb/Xt calculated from the above mentioned Xb and the above mentioned Xt is preferably $Xb/Xt \leq 0.32$, more preferably $Xb/Xt \leq 0.30$, and even more preferably $Xb/Xt \leq 0.28$, from the viewpoint of the handling properties of the composition. On the other hand, the lower limit of the Xb/Xt is not particularly limited, but from the viewpoint of maintaining good handling properties of the composition, the ratio is usually preferably $Xb/Xt \geq 0.22$, and more preferably $Xb/Xt \geq 0.24$.

The means for controlling the above mentioned value of Xb/Xt is not particularly limited, and a person skilled in the art can control it by optimizing the producing conditions appropriately according to known techniques. For example, the above mentioned value of Xb/Xt can be controlled by optimizing the reaction conditions of hydroformylation, the distillation conditions when distilling and purifying the obtained TCDDM composition, and the like.

The purity of the TCDDM composition of the present invention is not particularly limited as long as it satisfies the above mentioned Xc/Xt value, and the like. The TCDDM composition of the present invention may be one whose purity has been increased by purification or the like, or may contain impurities other than TCDDM.

In the TCDDM composition of the present invention, the lower limit of the content of tricyclodecane dimethanols is not particularly limited, but from the viewpoint of the handling properties of the composition, it is preferably 80% by mass or more, more preferably 90% by mass or more, and even more preferably 95% by mass or more, based on 100% by mass of a total mass of the TCDDM composition. On the other hand, the upper limit of the total content is not particularly limited, and the higher the content, the more preferable, and it may be 100% by mass, based on the total mass of the composition.

In the TCDDM composition of the present invention, the lower limit of a total content of the chiral compound A, the chiral compound B, and the chiral compound C is not particularly limited, but from the viewpoint of the handling properties of the composition, it is preferably 80% by mass or more, more preferably 90% by mass or more, and even more preferably 95% by mass or more, based on 100% by mass of a total mass of the composition. On the other hand, the upper limit of the total content is not particularly limited, and the higher the content, the more preferable, and it may be 100% by mass, based on the total mass of the composition.

<Production Method of TCDDM Composition>

The method for producing the above mentioned TCDDM composition is not particularly limited, but as one embodiment, the production method of the TCDDM composition of the present invention can be used.

The production method of the TCDDM composition of the present invention is a production method including a step of hydroformylating dicyclopentadiene to obtain tricyclodecane dicarbaldehydes, a step of obtaining a crude reaction solution containing tricyclodecane dimethanol by a reduction reaction of the tricyclodecane dicarbaldehyde, and a step of distilling and purifying the crude reaction solution to obtain a tricyclodecane dimethanol composition.

In this case, the tricyclodecane dicarbaldehydes which are precursors of the chiral compound A, the chiral compound B, and the chiral compound C respectively are obtained as a mixture, since isomers are generated in the process of introducing formyl groups by hydroformylation. After that, the chiral compound A, the chiral compound B, and the chiral compound C are obtained by the hydrogenation process.

There is no particular restriction on the method for controlling the ratio of the chiral compound A, the chiral compound B, and the chiral compound C of the present invention. The ratio may be controlled by adjusting the reaction conditions of hydroformylation, may be controlled by isomerization using a technique such as heating, or may be adjusted by distilling and purifying the produced TCDDM composition.

<Hydroformylation Reaction of Dicyclopentadiene>

There is no particular restriction on the method for hydroformylating dicyclopentadiene, and it can be carried out according to a conventional method.

For example, according to the method described in JP 2001-10999 A, tricyclodecane dicarbaldehyde can be produced by hydroformylating dicyclopentadiene using hydrogen and carbon monoxide in a hydroformylation reaction solvent comprising a hydrocarbon compound, in the presence of a catalyst comprising a rhodium compound and an organophosphorus compound, as shown in the following reaction formula (IV).

[Chem. 4]

(IV)

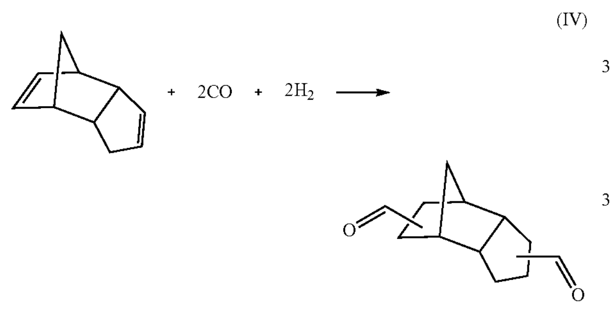

The rhodium compound used in this hydroformylation step may take any form of precursor, so long as it forms a complex with an organophosphorus compound and exhibits hydroformylation activity in the presence of hydrogen and carbon monoxide. That is, a catalytically active rhodium metal hydride carbonyl phosphorus complex may be formed in a reaction vessel by introducing a catalyst precursor such as $Rh(acac)(CO)_2$, $Rh_2O_3$, $Rh_4(CO)_{12}$, $Rh_6(CO)_{16}$, or $Rh(NO_3)_3$ into a reaction mixture together with an organic phosphorus compound, or a rhodium metal hydride carbonyl phosphorus complex catalyst may be prepared in advance and then introduced into the reaction vessel.

In a preferred embodiment of the present invention, $Rh(acac)(CO)_2$ is used as a rhodium precursor to react with an organophosphorus compound in the presence of a solvent, and then introduced into the reactor together with an excess of free organophosphorus compound to form a catalytically active rhodium-organophosphorus complex catalyst.

Organophosphorus compounds that form catalysts for the hydroformylation reaction with rhodium compounds include phosphites and phosphines.

Among these, the phosphite is preferably a compound represented by the general formula $P(—OR^1)(—OR^2)(—OR^3)$ (wherein $R^1$, $R^2$, and $R^3$ each represent an aryl group or alkyl group which may be substituted), since it is effective in the hydroformylation reaction of dicyclopentadiene. Specific examples of $R^1$, $R^2$, and $R^3$ include aryl groups such as phenyl group, naphthyl group, and the like which may be substituted with methyl group, ethyl group, isopropyl group, n-butyl group, t-butyl group, methoxy group, and the like; aliphatic alkyl groups such as methyl group, ethyl group, isopropyl group, n-butyl group, t-butyl group, and the like; alicyclic alkyl groups such as cyclopentyl group, cyclohexyl group, and the like which may be substituted with lower alkyl groups such as methyl group, ethyl group, isopropyl group, n-butyl group, t-butyl group; and the like.

Specific examples of suitable phosphites include, but are not limited to, tris(2-t-butylphenyl)phosphite, tris(3-methyl-6-t-butylphenyl)phosphite, tris(3-methoxy-6-t-butylphenyl) phosphite, tris(2,4-di-t-butylphenyl)phosphite, di(2-t-butylphenyl) (t-butyl)phosphite, and the like. These phosphites may be used alone or in combination of two or more.

As phosphines, alkylphosphines having large steric hindrance are particularly effective in the hydroformylation reaction of dicyclopentadiene. Representative examples include, but are not limited to, tricyclopropylphosphine, tricyclobutylphosphine, tricyclopentylphosphine, tricyclohexylphosphine, tricycloheptylphosphine, tricyclooctylphosphine, and the like. These phosphines may be used alone or in combination of two or more.

Tricyclodecane dicarbaldehyde can be obtained at a sufficient hydroformylation reaction rate, as long as the amount of the organic phosphorus compound used is in the range of 1 to 400 molar times, preferably 3 to 200 molar times, relative to the rhodium metal in the hydroformylation reaction solution.

The hydroformylation reaction of dicyclopentadiene can be carried out without using a solvent, but it can be carried out more preferably by using an organic solvent that is inert to the reaction.

As described below, after the hydroformylation reaction is completed, layer separation is performed. In this separation, the reaction product solution containing tricyclodecane dicarbaldehyde is contacted with alcohol, and tricyclodecane dicarbaldehyde is extracted into an extraction solvent layer consisting of alcohol while leaving the catalyst components in the dihydroformylation reaction solvent layer. For this reason, it is preferable to use a hydroformylation reaction solvent that separates into layers from the alcohol. Examples of such solvents include aromatic hydrocarbon compounds, aliphatic hydrocarbon compounds, and alicyclic hydrocarbon compounds.

Examples of the aromatic hydrocarbon compounds include methylbenzenes such as benzene, toluene, xylene, mesitylene pseudocumene, and the like, ethylbenzenes such as ethylbenzene, diethylbenzene, triethylbenzene, and the like, propylbenzenes such as isopropylbenzene, 1,3-diisopropylbenzene, 1,4-diisopropylbenzene, and the like. Various other alkylbenzenes can also be suitably used.

Examples of the aliphatic hydrocarbon compounds include pentane, hexane, heptane, octane, isooctane, dodecane, and decane, but are not limited to these as long as they are liquid at standard temperature and pressure.

Examples of the alicyclic hydrocarbon compounds include cyclohexane, cyclooctane, cyclododecane, decalin, methylcyclohexane, and the like.

These solvents may be used alone or in combination of two or more.

The solvent is preferably used so that the concentration of dicyclopentadiene in the reaction solution is 10 to 95% by mass, and particularly 30 to 90% by mass, from the viewpoint of reaction efficiency.

The amount of rhodium catalyst used is usually 10 to 5000 ppm by mass, more preferably 50 to 2000 ppm by mass, of rhodium metal based on the dicyclopentadiene of the raw material. When rhodium is used at 50 ppm or more, catalyst recovery is required.

The temperature and pressure of the hydroformylation reaction of dicyclopentadiene are usually 40 to 160° C., and preferably 80 to 140° C., and the reaction pressure is usually 1 to 15 MPa. When the temperature is lower than 40° C., the hydroformylation reaction rate is slow, and when it is higher than 160° C., side reactions will occur in the reaction solution from dicyclopentadiene and hydroformylation reaction products, resulting in a decrease in the aldehyde yield. When the pressure is lower than 1 MPa, the reaction rate of hydroformylation is slow, and when it is higher than 15 MPa, a high-pressure reaction apparatus is used, which increases the cost of the apparatus.

The molar ratio of hydrogen to carbon monoxide in the hydrogen/carbon monoxide mixed gas used in the reaction can be selected from the range of 0.2 to 5.0 as the introduction gas composition (hydrogen/carbon monoxide). When the hydrogen/carbon monoxide mixed gas is outside this range, the reaction activity of the hydroformylation reaction or the aldehyde selectivity decreases.

As the hydroformylation reaction method, a continuous feed method is adopted in which the raw material dicyclopentadiene is supplied alone or as a mixed solution of dicyclopentadiene and a solvent to a reactor containing a rhodium-organic phosphorus complex catalyst, a solvent, and a hydrogen/carbon monoxide mixed gas. This method reduces the generation of cyclopentadiene, which inhibits the hydroformylation reaction due to the thermal decomposition of dicyclopentadiene in the reactor, and maintains a good reaction rate and yield. In order to maintain the fluidity of dicyclopentadiene, it is preferable to dilute it with the above mentioned solvent and supply it to the reactor at a temperature at which depolymerization is not occurred and cyclopentadiene is not produced.

<Extraction of Tricyclodecane Dicarbaldehyde>

After the hydroformylation reaction is completed, layer separation is performed. In the separation, the reaction product solution is contacted with alcohol either as is or after dilution with the hydrocarbon compound used in the reaction as the hydroformylation reaction solvent or with another hydrocarbon compound, and the product tricyclodecane dicarbaldehyde is extracted into the alcohol while leaving the catalyst components in the hydroformylation reaction solvent layer.

Examples of alcohol include primary alcohols having 1 to 3 carbon atoms and polyhydric alcohols having 2 to 6 carbon atoms.

Examples of primary alcohols include methanol, ethanol, and propanol.

Examples of polyhydric alcohols having 2 to 6 carbon atoms include ethylene glycol, 1,3-propanediol, 1,2-propanediol, 1,4-butanediol, 1,2-butanediol, 1,3-butanediol, 2,3-butanediol, isomers of pentanediol, neopentyl glycol, hexanediol, glycerin, pentaerythritol, trimethylolpropane, and the like.

Among these, methanol, ethylene glycol, propanediol, and butanediol are preferably used because they have a relatively low boiling point, are inexpensive, and are easy to handle as liquids. These extraction solvents may be used alone or in combination of two or more.

Extraction may be performed in the presence of water in the alcohol. The addition of water makes it easier for the aldehyde and catalyst components to be distributed to each layer.

It is preferable that the reaction solvent and the extraction solvent used in the hydroformylation reaction have different densities in order to achieve effective layer separation. A suitable example of a combination of a hydroformylation reaction solvent containing tricyclodecane dicarbaldehyde and an extraction solvent is a combination of methylcyclohexane as the reaction solvent and ethylene glycol as the extraction solvent, or methylcyclohexane as the reaction solvent and methanol and water as the extraction solvent.

The distribution of tricyclodecane dicarbaldehyde between the hydroformylation reaction solvent and the extraction solvent is equilibrium. In contrast, rhodium and organophosphorus compounds as the catalyst components are substantially present only in the hydroformylation reaction solvent, and are present in the extraction solvent at levels below the analytical limit.

The volume ratio of the extraction solvent used to the reaction product solution is determined by the solubility of tricyclodecanedicarbaldehyde in the extraction solvent and the amount of tricyclodecanedicarbaldehyde to be extracted. For example, when the tricyclodecanedicarbaldehyde to be separated is highly soluble in the extraction solvent and exists in low concentration in the reaction product solution, practical extraction of tricyclodecanedicarbaldehyde is possible by using an extraction solvent with a low volume ratio (extraction solvent/reaction product solution).

The higher the concentration of the product, the higher the volume ratio (extraction solvent/reaction product solution) for extracting tricyclodecanedicarbaldehyde from the reaction product solution.

When tricyclodecanedicarbaldehyde has relatively low solubility in the extraction solution, the volume ratio (extraction solvent/reaction product solution) can vary in the range of 10:1 to 1:10. In order to increase the amount of tricyclodecanedicarbaldehyde extracted with a small amount of extraction solvent, it is effective to divide the extraction solvent and perform the extraction operation several times. In the final extraction step, a hydroformylation reaction solvent such as methylcyclohexane may be added in an amount of about 5 to 20 mass % based on the reaction product solution. The addition of the hydroformylation reaction solvent can improve the catalyst removal rate.

There is no particular restriction on the temperature at which the extraction operation is carried out, but it is practical to carry out the operation at a temperature equal to or lower than the hydroformylation reaction. After the reaction, an extraction operation may be carried out by adding an extraction solvent to the hydroformylation reactor, or the hydroformylation reaction product solution may be withdrawn from the hydroformylation reactor and the operation may be carried out in an extraction tank. It is also possible to carry out the extraction operation by directly adding an extraction solvent to the hydroformylation reactor and retaining the catalyst components in the hydroformylation reactor as is to carry out the next hydroformylation reaction. When the hydroformylation reaction product solution is withdrawn and the operation is carried out in an extraction tank, the reaction solvent layer of the catalyst-containing hydrocarbon compound is returned to the hydroformylation reactor and used again in the reaction. This process can be carried out as a batch process or a continuous process.

In the above mentioned extraction operation, a tricyclodecane dicarbaldehyde-containing solution containing 10 to 90% by mass of tricyclodecane dicarbaldehyde and 10 to 90% by mass of an extraction solvent can be obtained. When a reaction solvent is added, a tricyclodecanedicarbaldehyde-containing solution containing 5 to 90% by mass of tricyclodecanedicarbaldehyde, 5 to 90% by mass of an extraction solvent, and 5 to 90% by mass of the reaction solvent can be obtained.

The alcohol of the extraction solvent reacts with a part of the hydroformylation product tricyclodecanedicarbaldehyde to produce an acetal compound in which tricyclodecanedicarbaldehyde is acetalized.

The content of acetal compounds in tricyclodecanedicarbaldehyde is usually about 0.1 to 50% by mass, and more preferably about 1 to 25% by mass.

<Hydrogenation Reduction Reaction>

The extract containing tricyclodecanedicarbaldehyde obtained by the above extraction operation (tricyclodecanedicarbaldehyde-containing solution) is then hydrogenated and reduced in the presence of a hydrogenation catalyst, preferably a ruthenium (Ru) catalyst, to produce TCDDM as shown in the following reaction formula (V).

This hydrogenation reduction reaction is preferably carried out in the presence of water and a Ru catalyst, whereby the acetal compound is rapidly converted to tricyclodecane dicarbaldehyde during the hydrogenation reaction of tricyclodecane dicarbaldehyde, and the tricyclodecane dicarbaldehyde converted from the acetal compound is hydrogenated to produce TCDDM in a high yield.

[Chem. 5]

(V)

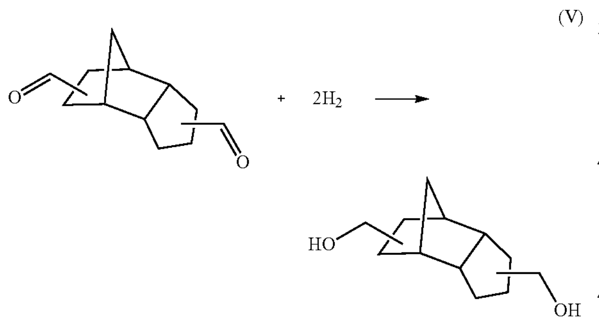

The amount of water present in the hydrogenation reduction reaction is preferably equal to or more than the amount of acetal compound in the hydrogenation reduction reaction solution, and is preferably an amount that does not cause phase separation of the reaction solution. The water content of the total reaction solution is 2% by mass or more, preferably 2 to 30% by mass, more preferably 5 to 25% by mass, and particularly preferably 10 to 20% by mass. When the water content is within the above range, water and the reaction solvent do not separate into layers, and the above mentioned effect of having water present in the hydrogenation reaction system can be effectively obtained. The water may be added in an extraction step in which the catalyst components and tricyclodecane dicarbaldehyde are separated from the hydroformylation reaction product solution, or water may be added to the reaction system immediately before the hydrogenation reduction reaction.

In one reaction form, the catalyst is charged as a slurry in a stirred reactor, the reaction is carried out in a batchwise manner, and after the reaction, the catalyst is separated from the product solution by settling and filtration. In another reaction form which is a flood reaction method, a molded catalyst is charged in a tubular reactor and the product solution and hydrogen gas are passed over the catalyst, may be appropriately adopted. There is no particular restriction on the amount of catalyst used as long as TCDDM can be produced with industrially advantageous productivity.

The reaction temperature and pressure of the hydrogenation reduction reaction are usually 40 to 200° C., and preferably 70 to 150° C., and the reaction pressure is usually 15 MPa or less. When the temperature is lower than 40° C., the hydrogenation reduction reaction rate is slow, and when the temperature is higher than 200° C., side reactions from the target TCDDM proceed, reducing the yield of TCDDM. When the pressure is higher than 15 MPa, a high-pressure reaction apparatus is used, which increases the cost of the apparatus.

<Removal of Residual Metals>

The crude reaction solution obtained by the above hydrogenation reduction reaction operation contains metal elements derived from the hydrogenation catalyst as eluted components. By removing the metal elements from the crude reaction solution prior to distillation and purification, it is possible to suppress the thermal decomposition of TCDDM caused by the metal elements in the distillation and purification step.

There are no particular limitations on the method for removing metal elements from the crude reaction solution to reduce their content, and examples thereof include treatment with activated carbon, cation exchange resin, silica gel adsorption, and the like. Activated carbon treatment is preferred because of its removal efficiency and the ability to reuse the adsorbent.

The activated carbon treatment method may be a batch treatment in which activated carbon is added to the crude reaction solution and stirred, and then the activated carbon is filtered or the like to separate the solid and liquid, or a continuous treatment in which the crude reaction solution is passed through an activated carbon packed tower.

In the case of the batch treatment, the amount of activated carbon added to the crude reaction solution is appropriately determined depending on the metal element adsorption capacity of the activated carbon, the metal element content in the crude reaction solution, and the like. As a general condition, it is preferable to add activated carbon to the crude reaction solution so as to give a concentration of about 0.01 to 10% by mass, and stir the mixture.

In the case of continuous treatment, the treatment flow rate is not particularly limited, but it may be 1 to 10 in terms of a space velocity (LHSV).

Such activated carbon treatment may be performed multiple times. That is, the activated carbon treated solution obtained by treating the crude reaction solution with activated carbon may be treated with activated carbon again. In this case, the type and amount of activated carbon used, the processing conditions, and the like. used in the first activated carbon treatment and the second activated carbon treatment may be different.

The lower the metal element content of the crude reaction solution to be subjected to the distillation and purification in the next step, the more preferable it is from the viewpoint of suppressing the thermal decomposition of TCDDM. The metal element content of the crude reaction solution to be subjected to distillation and purification is preferably 10 ppm by mass or less, and preferably 5 ppm by mass or less, and especially preferably 1 ppm by mass or less.

The pH of the crude reaction solution to be subjected to distillation and purification is preferably in the range of 6 to 8. It is preferable that the lower limit of the pH is 6 or more, since the by-production of low boiling point compounds thought to be caused by dehydration of TCDDM and the by-production of high boiling point compounds thought to be caused by dimerization such as etherification can be suppressed. It is preferable that the upper limit of the pH is 8 or less, since the distillation and purification equipment is less susceptible to alkali corrosion.

The pH of the reaction product solution obtained by the hydrogenation reduction reaction is usually 6 to 8, and the pH hardly changes even when it is subjected to the hydrogenation catalyst removal treatment and the metal element removal treatment. But the pH may deviate from the range of 6 to 8 due to acid and alkali components eluted from the hydrogenation catalyst. In this case, it is preferable to adjust the pH to 6 to 8 by adding a pH adjuster such as an acid or alkali as appropriate.

<Distillation>

The crude reaction solution having reduced metal element content is then subjected to distillation and purification.

This distillation and purification is preferably carried out using a distillation tower having a number of theoretical plate of 10 to 30 and a bottom temperature in the range of 150 to 250° C.

When the number of theoretical plate of the distillation tower used for distillation and purification is 10 or more, impurities and products can be easily separated, and when it is 30 or less, the pressure difference between the top and bottom of the tower is small and the temperature of the bottom of the tower is low, so the heat load of the equipment is small. A more preferable number of theoretical plate is 15 to 30.

When the bottom temperature is 150° C. or higher, TCDDM can be volatilized, and when it is 250° C. or lower, the by-production of high boiling impurities due to dimerization of TCDDM can be suppressed. A more preferable bottom temperature is 160 to 230° C.

There are no particular limitations on other distillation tower conditions in distillation and purification, but it is usually carried out at a pressure of 0.1 to 100 kPa and a reflux ratio of about 1 to 30. In particular, by controlling the reflux ratio and distillate amount, it becomes possible to adjust the abundance ratios of the chiral compound A, the chiral compound B, and the chiral compound C in the resulting TCDDM composition. These conditions may be arbitrarily changed depending on the equipment performance, pot efficiency, recovery amount, and the like of the distillation tower, and there are no particular limitations as long as a TCDDM composition having the composition specified in the present invention is obtained.

The bottom solution of the distillation tower obtained by such distillation and purification may be further subjected to simple distillation at 0.1 to 10 kPa and 140 to 250° C. By such distillation and purification, a TCDDM composition having a TCDDM purity of 98% or more can be obtained in high yield.

<Ultraviolet Curable Composition>

The ultraviolet curable composition of the present invention is an ultraviolet curable composition derived from the TCDDM composition of the present invention.

More specifically, the ultraviolet curable composition of the present invention is an ultraviolet curable composition synthesized using the TCDDM composition of the present invention as a raw material. More specifically, the ultraviolet curable composition of the present invention is an ultraviolet curable composition synthesized using the tricyclodecane dimethanols contained in the TCDDM composition of the present invention as a raw material.

The method for producing the ultraviolet curable composition is not particularly limited, and can be carried out according to a conventional method. In general, it is desirable to use the tricyclodecane dimethanols in the TCDDM composition as a raw material to produce a derivative such as a di(meth)acrylic acid ester derivative, a urethane acrylate, or the like.

Both of the two hydroxyl groups of the tricyclodecane dimethanols contained in the TCDDM composition may be used in the reaction, or one of the hydroxyl groups may be reacted and the other hydroxyl group may be left. In this case, the remaining hydroxyl group may be appropriately converted to a functional group suitable for the application by an organic synthesis method.

Specific examples of methods for producing di(meth) acrylic acid ester derivatives from TCDDM using the TCDDM composition as a raw material include a method of reacting TCDDM with (meth)acrylic acid, a method of transesterifying TCDDM with a (meth)acrylic acid ester, a method of reacting TCDDM with a halide of (meth)acrylic acid such as (meth)acrylic acid chloride, and the like.

The reaction conditions for each of the above production methods are as follows.

When producing a di(meth)acrylic acid ester derivative using (meth)acrylic acid or a (meth)acrylic acid ester, the reaction can be accelerated by using a catalyst and continuously removing the water or lower alcohol produced from the system.

Examples of the catalyst include known esterification catalysts such as sulfuric acid, paratoluenesulfonic acid, boron trifluoride, organotin compounds, and the like, and any of these can be selected and used. From the viewpoints of reducing the load on the production equipment and reducing catalyst costs, the amount of catalyst used is preferably 10 to 100,000 ppm based on a total mass of the reaction substrates.

When producing a di(meth)acrylic acid ester derivative using a halide of (meth)acrylic acid, the reaction is preferably carried out in the presence of a basic compound, and the reaction can also be accelerated by using a catalyst.

Examples of the basic compound include known basic compounds such as tertiary amines such as triethylamine, N-ethyldiisopropylamine, and the like, phosphates such as potassium phosphate, sodium phosphate, and the like, carbonates such as potassium carbonate, sodium carbonate, and the like, and hydroxides such as potassium hydroxide, sodium hydroxide, and the like, and any of these may be arbitarily selected and used. The amount of the basic compound used is preferably 1.0 to 6.0 equivalents based on 1 equivalent of acrylic acid or methacrylic acid halide, from the viewpoints of reducing the load on the production equipment, reducing raw material costs, and the like.

Examples of the catalyst include catalysts known for the esterification reaction of acid chlorides, such as pyridines such as N,N-dimethyl-4-aminopyridine, and the like, imidazoles such as N-methylimidazole, and the like, and tertiary amines such as triethylenediamine, and the like, and any of these may be arbitarily selected and used. The amount of the catalyst used is preferably 10 to 100,000 ppm based on a total mass of the reaction substrates, from the viewpoints of reducing the load on the production equipment, reducing catalyst costs, and the like.

In each of the above mentioned producing methods, it is preferable to add a polymerization inhibitor to prevent thermal polymerization of (meth)acrylic acid, (meth)acrylic acid esters, or (meth)acrylic acid halides.

Examples of the polymerization inhibitor include hydroquinone, paramethoxyphenol, 2,4-dimethyl-6-t-butylphenol, 3-hydroxythiophenol, α-nitroso-β-naphthol, parabenzoquinone, 2,5-dihydroxyparabenzoquinone, copper salts, phenothiazine, paraphenylenediamine, phenyl-β-naphthylamine, and the like. The amount of the polymerization inhibitor used is preferably 10 to 100,000 ppm based on a total mass of the reaction substrates, from the viewpoints of catalyst activity, reducing the effect on side reactions, and the like.

In each of the above mentioned producing methods, the reaction temperature is preferably −20 to 120° C., and more preferably 0 to 100° C., from the viewpoints of shortening the reaction time and preventing polymerization. The reaction time is preferably 1 to 20 hours.

A solvent can also be used in the reaction in each of the above mentioned producing methods.

The solvent is not particularly limited as long as it does not adversely affect the reaction. Examples of the solvent include aromatic hydrocarbons such as benzene, toluene, xylene, ethylbenzene, mesitylene, and the like; aliphatic hydrocarbons such as pentane, hexane, heptane, octane, nonane, decane, cyclohexane, cyclooctane, and the like; halogenated hydrocarbons such as dichloromethane, chloroform, 1,2-dichloroethane, carbon tetrachloride, chlorobenzene, trifluoromethylbenzene, and the like; ethers such as diethyl ether, diisopropyl ether, dibutyl ether, anisole, tetrahydrofuran, dioxane, and the like; ketones such as methyl ethyl ketone, diethyl ketone, methyl isobutyl ketone, and the like; esters such as ethyl acetate, isopropyl acetate, and the like; nitriles such as acetonitrile, and the like; acyclic or cyclic amides such as dimethylformamide, N-methylpyrrolidinone, and the like; and acyclic or cyclic sulfoxides such as dimethyl sulfoxide, and the like, or sulfones. These solvents may be used alone or in combination of two or more.

The structure of the urethane acrylate made from the TCDDM composition is not particularly limited, so long as it is an acrylic acid or methacrylic acid ester derivative containing a urethane bond.

Specifically, a method for producing a urethane acrylate from TCDDM using the TCDDM composition as a raw material is preferably a method in which the TCDDM composition, a polyisocyanate compound, and a monohydroxyacrylate compound are reacted in the presence of a catalyst. In addition, a polyol compound other than the TCDDM composition may be further added for the purpose of adjusting the performance of the cured product.

The content ratio of the TCDDM composition to the total mass of the reaction substrate as the urethane acrylate raw material is preferably 10% by mass or more, more preferably 20% by mass or more, and even more preferably 30% by mass or more, from the viewpoints of the hardness and heat resistance of the cured product. On the other hand, there is no particular upper limit to the content ratio, and the higher the content ratio, the better.

Examples of the polyisocyanate compound include paraphenylene diisocyanate, 2,4-tolylene diisocyanate, 2,6-tolylene diisocyanate, 2,2'-diphenylmethane diisocyanate, 2,4-diphenylmethane diisocyanate, 4,4'-diphenylmethane diisocyanate, diphenylether-4,4'-diisocyanate, o-xylylene diisocyanate, m-xylylene diisocyanate, p-xylylene diisocyanate, norbornene methane diisocyanate and their hydrogenated derivatives, pentamethylene diisocyanate, hexamethylene diisocyanate, dicyclohexylmethane diisocyanate, 1,4-cyclohexane diisocyanate, isophorone diisocyanate, and the like. Nurates, adducts, and biuret forms of these compounds may also be used, as well as dimers and trimers. These may be used alone or in combination of two or more.

It is preferable that the structural moiety of the monohydroxyacrylate compound that bonds the hydroxy group and the acryloyloxy group is composed of three carbon atoms or more. Examples of such compounds include acrylates of aliphatic polyols having 3 or more carbon atoms, such as hydroxypropyl acrylate, trimethylolpropane diacrylate, pentaerythritol triacrylate, ditrimethylolpropane triacrylate, dipentaerythritol pentaacrylate, and the like; (poly)oxyalkylene modified compounds in which a (poly)oxyalkylene chain, such as a (poly)oxyethylene chain, a (poly)oxypropylene chain, a (poly)oxytetramethylene chain or the like, has been introduced into the molecular structure of the above mentioned acrylate compound; lactone modified compounds in which a (poly)lactone structure has been introduced into the molecular structure of the above mentioned acrylate compound; isocyanuric acid diacrylates; (poly)oxyalkylene modified compounds in which a (poly)oxyalkylene chain, such as a (poly)oxyethylene chain, a (poly)oxypropylene chain, a (poly)oxytetramethylene chain or the like, has been introduced into the molecular structure of the isocyanuric acid diacrylate; lactone modified compounds in which a (poly)lactone structure has been introduced into the molecular structure of the isocyanuric acid diacrylate, and the like. Also, methacrylate compounds in which the acrylate in the above mentioned compound group is replaced with methacrylate may be used. These may be used alone or in combination of two or more.

Examples of polyol compounds other than the TCDDM composition include linear diols such as ethylene glycol, 1,3-propanediol, 1,4-butanediol, 1,5-pentanediol, 1,6-hexanediol, and the like; branched diols having a branched chain such as 2-methyl-1,3-propanediol, 2,2-dimethyl-1,3-propanediol, 1,4-dimethylolhexane, 2-ethyl-1,3-hexanediol, 2,2,4-trimethyl-1,3-pentanediol, dimer diol, and the like; diols having an ether group such as diethylene glycol, propylene glycol, and the like; diols having an alicyclic structure such as 1,4-cyclohexanediol, 1,4-cyclohexanedimethanol, 1,4-dihydroxyethylcyclohexane, and the like; diols having an aromatic group such as xylylene glycol, 1,4-dihydroxyethylbenzene, 4,4'-methylenebis(hydroxyethylbenzene), and the like; polyols such as glycerin, trimethylolpropane, pentaerythritol, and the like; polyether polyols, polyester polyols, polycarbonate polyols, and the like. These polyol compounds may be used alone or in combination of two or more.

Examples of the catalyst include organic tin compounds such as dibutyltin dilaurate, trimethyltin hydroxide, tetra-n-butyltin, and the like; organic bismuth compounds such as dibutyl bismuth dilaurate, dioctyl bismuth dilaurate, and the like; metal salts such as zinc octoate, tin octoate, cobalt naphthenate, stannous chloride, stannic chloride, and the like; and amine catalysts such as triethylamine, benzyldiethylamine, 1,4-diazabicyclo[2,2,2]octane, 1,8-diazabicyclo[5,4,0]undecene, N,N,N',N'-tetramethyl-1,3-butanediamine, N-ethylmorpholine, and the like.

In order to prevent thermal polymerization of monohydroxyacrylate compounds and the like, it is preferable to add a polymerization inhibitor.

The polymerization inhibitor is not particularly limited as long as it does not inhibit the reaction, and examples include hydroquinone, paramethoxyphenol, 2,4-dimethyl-6-t-butylphenol, 3-hydroxythiophenol, α-nitroso-β-naphthol, parabenzoquinone, 2,5-dihydroxyparabenzoquinone, copper salt, phenothiazine, paraphenylenediamine, phenyl-β-naphthylamine, and the like. The amount of the polymerization inhibitor used is preferably 10 to 100,000 ppm based on the total mass of the reaction substrates, from the viewpoints of catalytic activity and reducing the influence on side reactions.

In the above mentioned producing method, the reaction temperature is preferably 30 to 120° C., and more preferably 40 to 100° C., from the viewpoints of shortening the reaction time and preventing polymerization. The reaction time is preferably 1 to 10 hours.

A solvent can also be used in the reaction in each of the above mentioned producing methods.

The solvent is not particularly limited as long as it does not adversely affect the reaction. Examples of the solvent include aromatic hydrocarbons such as benzene, toluene, xylene, ethylbenzene, mesitylene, and the like; aliphatic hydrocarbons such as heptane, octane, nonane, decane, cyclohexane, cyclooctane, and the like; halogenated hydrocarbons such as dichloromethane, chloroform, 1,2-dichloroethane, carbon tetrachloride, chlorobenzene, trifluoromethylbenzene, and the like; ethers such as diisopropyl ether, dibutyl ether, anisole, tetrahydrofuran, dioxane, and the like; ketones such as methyl ethyl ketone, diethyl ketone, methyl isobutyl ketone, and the like; esters such as ethyl acetate, isopropyl acetate, and the like; nitriles such as acetonitrile, and the like; acyclic or cyclic amides such as dimethylformamide, N-methylpyrrolidinone, and the like; and acyclic or cyclic sulfoxides such as dimethyl sulfoxide, and the like, or sulfones. These solvents may be used alone or in combination of two or more.

The ultraviolet curable composition of the present invention is synthesized using the TCDDM composition of the present invention as a raw material, and therefore can be controlled to a high viscosity without impairing the performance originally required of the ultraviolet curable composition, and has excellent coating stability. For this reason, the ultraviolet curable composition of the present invention can be suitably used as hard coating materials, antifouling coating materials, resist materials, inkjet inks, materials for 3D printers, and the like.

In applications to resists and the like, a method is used in which the ultraviolet curable composition is applied to a substrate using a screen printing method or a flex printing method, and then cured. From the viewpoints of being able to apply thin and uniformly, being able to apply thickly, and being able to print fine patterns on a substrate with high precision, the ultraviolet curable composition is required to have a high viscosity.

In applications to hard coats, antifouling coats, inkjet printing, and the like, a method is used in which the ultraviolet curable composition is applied to a substrate using a coater method, a spray method, or a dispenser method, and then cured. From the viewpoint of accurately discharging a fixed amount of the ultraviolet curable composition, the ultraviolet curable composition is required to have a high viscosity.

As described above, the ultraviolet curable composition of the present invention is derived from the TCDDM composition that is mainly composed of three types of enantiomers having different bonding positions of the hydroxymethyl group, so that it is less prone to stringiness and has excellent handling properties, by adjusting the crystallinity by appropriately controlling the isomer ratio. Therefore, the ultraviolet curable composition of the present invention has a high viscosity and is excellent in coating stability and application stability. Furthermore, since there is no need to add a viscosity improver to increase the viscosity, there is no problem that the performance originally required to the ultraviolet curable composition is impaired. For these reasons, the ultraviolet curable composition of the present invention can be suitably used for applications such as hard coating materials, antifouling coating materials, resist materials, inkjet inks, and materials for 3D printers.

<Polymer Composition>

The polymer composition of the present invention is a polymer composition derived from the TCDDM composition of the present invention, or a polymer composition derived from the ultraviolet curable composition of the present invention.

More specifically, the polymer composition of the present invention is a polymer composition obtained by polymerizing the TCDDM composition of the present invention or a composition containing the TCDDM composition, and is a composition containing a polymer containing structural units derived from tricyclodecane dimethanols in the TCDDM composition. Alternatively, the polymer composition of the present invention is a composition containing a polymer obtained by polymerizing the ultraviolet curable composition of the present invention.

One embodiment of the polymer composition of the present invention may be the polymer composition itself, or may be a composition obtained by adding or removing an appropriate amount of a solvent such as water or an organic solvent to adjust the solid content concentration, or may be a solid obtained by removing the solvent and drying. Furthermore, it may be a polymer composition obtained by purifying a composition containing a polymer obtained by polymerization by appropriately removing impurities, or may be a polymer composition obtained by adding appropriate additives such as storage stabilizers (such as ultraviolet absorbers and antioxidants), colorants, antistatic agents, lubricants, fillers, flame retardants, foaming agents, and the like, as necessary, within a range that does not affect the performance of the polymer obtained by polymerization.

In other words, the polymer composition of the present invention may be any composition containing a polymer obtained by polymerizing the TCDDM composition of the present invention or the ultraviolet curable composition of the present invention, and is not particularly limited with respect to its form or component composition.

Specific examples of other embodiments of the polymer composition include at least one selected from the group consisting of polyester resins, epoxy resins, acrylate resins, polycarbonate resins, and polyurethane resins.

In the present invention, the polyester resin is a resin mainly composed of a polyethylene-based polymer such as polyethylene terephthalate (PET). The polyethylene-based polymer is not particularly limited, and examples thereof include polymers that contain a structural unit derived from a polyol mainly composed of a glycol and a structural unit derived from a terephthalic acid-based compound, and also contain a structural unit derived from the tricyclodecane dimethanols in the TCDDM composition of the present invention.

In the present invention, the epoxy resin is a resin mainly composed of an epoxy-based polymer. The epoxy-based polymer is not particularly limited, and examples thereof include polymers that contain a structural unit derived from a bisphenol-based compound and a structural unit derived from epichlorohydrin, and also contain structural units derived from the tricyclodecane dimethanols in the TCDDM composition of the present invention.

In the present invention, the acrylate resin is a resin mainly composed of an acrylate-based polymer. The acrylate-based polymer is not particularly limited, and examples thereof include polymers that contain a structural unit derived from (meth)acrylic acid or a structural unit derived from (meth)acrylic acid derivatives, and also contain structural units derived from tricyclodecane dimethanols in the TCDDM composition of the present invention.

In the present invention, the polycarbonate resin is a resin mainly composed of a polycarbonate-based polymer. The polycarbonate-based polymer is not particularly limited, and examples thereof include polymers that contain a structural unit derived from a bisphenol-based compound, and a structural unit derived from a phosgene (carbonyl chloride), or a structural unit derived from diphenyl carbonate, and also contain a structural unit derived from tricyclodecane dimethanols in the TCDDM composition of the present invention.

In the present invention, the polyurethane-based resin is a resin mainly composed of a polyurethane-based polymer. The polyurethane-based polymer is not particularly limited, and examples thereof include polymers that contain a structural unit derived from a polyol mainly composed of a glycol, and a structural unit derived from a bifunctional isocyanate, and also contain structural units derived from tricyclodecane dimethanols in the TCDDM composition of the present invention.

EXAMPLES

Hereinafter, the present invention will be explained in further detail with reference to Examples. The present invention is not limited to the following Examples.

The compounds used in the Examples and Comparative Examples are as follows.

- Dicyclopentadiene (manufactured by Fujifilm Wako Pure Chemical Corporation)
- Acetylacetonatodicarbonylrhodium (manufactured by N.E. Chemcat Corporation)
- Tris(2,4-di-tert-butylphenyl)phosphite (manufactured by Tokyo Chemical Industry Co., Ltd.)
- Methylcyclohexane (manufactured by Fujifilm Wako Pure Chemical Corporation)
- Ruthenium-supported carbon (dry basis Ru content 5%, water content 56%) (product name: Ru/C, manufactured by N.E. Chemcat Corporation)
- Powdered activated carbon (product name: Specialty Shirasagi, manufactured by Osaka Gas Chemicals Co., Ltd.)

Evaluations in the Examples and Comparative Examples were carried out by the following methods.

<Measurement of Xa, Xb, Xc, and Xt>

For the TCDDM compositions obtained in the Examples and Comparative Examples, the peak area Xa of the chiral compound A, the peak area Xb of the chiral compound B, the peak area Xc of the chiral compound C, and the total peak areas Xt of TCDDM were calculated using a gas chromatography according to the following procedure.

<Gas Chromatography Analysis Conditions>

- Measuring device: GC-2025 (manufactured by Shimadzu Corporation)
- Carrier gas: Helium, linear velocity 30 cm/sec
- Column: DB-1 (manufactured by Agilent Technologies, length 30 m×inner diameter 0.25 mm×film thickness 1.00 μm)
- Temperature (temperature rising conditions): 160° C.→heat up at 5° C./min→300° C. (holding time 2 min)
- Inlet temperature: 200° C.
- Ion source temperature: 300° C.
- Sample volume: 0.3 μL
- Split ratio: 1:30
- Detector: FID The gas chromatogram of the TCDDM composition obtained in following Example 3 is shown in FIG. 1.

The peak labeled (1) and having an elution time between 14.88 minutes and 15.03 minutes ("Peak 1") is the peak of the chiral compound A in the TCDDM composition.

The peak labeled (2) and having an elution time between 15.03 minutes and 15.18 minutes ("Peak 2") is the peak of the chiral compound B in the TCDDM composition.

The peak labeled (3) and having an elution time between 15.38 minutes and 15.56 minutes ("Peak 3") is the peak of the chiral compound C in the TCDDM composition.

The small unlabeled peaks are the peaks of the other TCDDM isomers.

The peak areas Xa, Xb, Xc, and Xt were determined according to the following procedure.

The area between the baseline and the gas chromatogram curve in the obtained gas chromatogram in the range of elution times from 14.88 to 15.90 minutes was defined as Xt.

The area between the baseline and the gas chromatogram curve in the obtained gas chromatogram in the range of elution times from 14.88 to 15.03 minutes was defined as Xa.

The area between the baseline and the gas chromatogram curve in the obtained gas chromatogram in the range of elution times from 15.03 to 15.18 minutes was defined as Xb.

The area between the baseline and the gas chromatogram curve in the obtained gas chromatogram in the range of elution times from 15.38 to 15.56 minutes was defined as Xc.

<Mass Analysis of TCDDM Composition>

The m/z and fragment pattern of the TCDDM compositions obtained in the Examples and Comparative Examples were measured using a gas chromatography mass spectrometry according to the following procedure.

<Gas Chromatography Mass Spectrometry Conditions>

- Measuring device: GCMS-QP2010Ultra (manufactured by Shimadzu Corporation)
- Carrier gas: Helium, linear velocity 40 cm/sec
- Column: BPX-5 (manufactured by Trajan Scientific and Medical, length 60 m×inner diameter 0.32 mm×film thickness 0.25 μm)
- Temperature (temperature rising conditions): 160° C.→heat up at 5° C./min→300° C. (holding time 2 min)
- Vaporization chamber temperature: 200° C.
- Ion source temperature: 250° C.
- MS interface temperature: 300° C.
- Injection volume: 0.5 μL
- Split ratio: 1:30

<Evaluation of Handling Properties>

As an index of handling properties of the TCDDM compositions obtained in the Examples and Comparative Examples, a tip of a glass rod was immersed 10 mm into a test liquid at room temperature (20° C.) and a stringiness when it was raised 10 cm was evaluated according to the following criteria.

<Criteria>

- A: No stringiness was observed.
- B: Stringiness was observed, but the thread broke immediately.

C: Stringiness was observed, and the thread remained without breaking.

Reference Example 1

<Hydroformylation Reaction>

In an autoclave reactor having a capacity of 20 L, 2.51 g of Rh(acac)$(CO)_2$ and 188.6 g of tris(2,4-di-tert-butylphenyl)phosphite were weighed out as raw material compounds for the hydroformylation reaction catalyst under a nitrogen atmosphere, and 3.9 kg of methylcyclohexane was charged as an organic solvent. The temperature of the reaction solution in the reactor was then raised to 70° C. while stirring at 120 rpm. Next, a mixed gas of hydrogen and carbon monoxide (hydrogen:carbon monoxide=1:1 (molar ratio)) was quickly injected from the gas inlet valve so that the pressure in the reactor was 5 MPaG. While maintaining this pressure, the temperature of the reaction solution was raised to 100° C., and 4.9 kg of dicyclopentadiene was further fed as a raw material compound over a period of 5 hours, and the reaction was allowed to proceed for another 3 hours. During the reaction, the amount of mixed gas consumed in the reaction was continuously introduced into the reactor so as to maintain the pressure in the reactor at 5 MPaG.

After the reaction was completed, the reaction solution in the reactor was cooled to room temperature, and the remaining gas in the reactor was released to obtain 12.5 kg of hydroformylation reaction product solution. The amount of dicyclopentadiene, the raw material compound contained in the reaction solution before the reaction, and the amount of tricyclodecane dicarbaldehyde, the product in the reaction product solution after the reaction, were analyzed by a gas chromatography to determine the yield of tricyclodecane dicarbaldehyde. The yield was 99%.

<Extraction Operation>

3.77 kg of methanol and 2.0 kg of water were added to the 12.5 kg of obtained hydroformylation reaction product solution, and the mixture was stirred for 30 minutes under a nitrogen atmosphere. After that, the mixture was left to stand for 30 minutes to separate into two phases, and an extraction operation was performed. 0.4 kg of methylcyclohexane was added to the obtained lower phase (a1) and stirred for 30 minutes. After that, the mixture was left to stand for 30 minutes to separate into two phases, and an extraction operation was performed to obtain 13.8 kg of the lower phase (a2).

The composition of the obtained lower phase (a2) was analyzed by a gas chromatography, and it was found to be 47% by mass of tricyclodecane dicarbaldehyde, 27% by mass of methanol, 14% by mass of water, 7% by mass of methylcyclohexane, and 5% by mass of other components.

<Hydrogenation Reduction Reaction>

After 13.8 kg of the lower phase (a2) obtained by the above mentioned extraction operation and 0.14 kg of ruthenium-supported carbon were charged into an autoclave reactor having a capacity of 20 L, the temperature of the reaction solution in the reactor was raised to 160° C. while stirring at 120 rpm. Next, hydrogen gas was injected from the gas inlet valve so that the pressure in the reactor was 5 MPaG, and the reaction was performed for 8 hours while maintaining this pressure and the temperature of the reaction solution. During the reaction, the amount of mixed gas consumed in the reaction was continuously introduced into the reactor so as to maintain the pressure in the reactor at 5 MPaG.

After the reaction was completed, the reaction solution in the reactor was cooled to room temperature, the remaining gas in the reactor was released, and the ruthenium-supported carbon was separated by filtration using a 5 μm filter to obtain 14.5 kg of reaction product solution. The amount of tricyclodecane dicarbaldehyde, the raw material compound contained in the reaction solution before the reaction, and the amount of TCDDM, the product in the reaction product solution after the reaction, were analyzed by a gas chromatography. The yield of TCDDM was 94%.

The Ru concentration of the reaction product solution analyzed by an X-ray fluorescence analysis was 36 ppm by mass. The pH of the reaction product solution was 7.

Example 1

1.90 kg of the hydrogenation reduction reaction product solution obtained in Reference Example 1 was charged into a batch distillation tower packed with structured packings equivalent to 20 theoretical stages. After 1.03 kg of low-boiling components mainly composed of the solvent were distilled off, the TCDDM composition was distilled at 0.4 kPa and 185° C., and the initial distillate and main distillate were recovered in that order. The amount of the TCDDM composition recovered as the main distillate was 0.36 kg. The obtained TCDDM composition was evaluated for the component ratios of the chiral compound A, the chiral compound B, and the chiral compound C, as well as for its handling properties. The evaluation results are shown in Table 1.

Example 2

The hydrogenation reduction reaction product solution obtained in Reference Example 1 was subjected to simple distillation at 0.3 kPa and 210° C. to obtain a TCDDM composition. The obtained TCDDM composition was evaluated for the component ratios of the chiral compound A, the chiral compound B, and the chiral compound C, as well as for its handling properties. The evaluation results are shown in Table 1.

Example 3

1.00 kg of the hydrogenation reduction reaction product solution obtained in Reference Example 1 was added with powdered activated carbon to a concentration of 1% by mass, and stirred at room temperature for 3 hours. The stirred reaction product solution was then filtered to remove the powdered activated carbon, and 0.95 kg of activated carbon-treated solution was obtained. The Ru concentration of the activated carbon-treated solution analyzed by an X-ray fluorescent analysis was 3.5 ppm by mass.

0.12 kg of this activated carbon-treated solution was charged into a batch distillation tower packed with structured packings equivalent to 20 theoretical stages, and after distilling off the solvent, distillation was performed at 0.6 kPa, 185° C., and a reflux ratio of 30 until 17 g was distilled. Furthermore, 0.01 kg of the obtained bottom solution was subjected to simple distillation at 0.3 kPa and 210° C. to obtain 0.01 kg of TCDDM composition. The obtained TCDDM composition was evaluated for the component ratios of the chiral compound A, the chiral compound B, and the chiral compound C, as well as for its handling properties. The evaluation results are shown in Table 1.

Comparative Example 1

The content ratios of the chiral compound A, the chiral compound B, and the chiral compound C, and the handling properties of a commercially available TCDDM composition (1) (product name: TCD Alcohol DM, manufactured by OQ Chemicals) were evaluated. The evaluation results are shown in Table 1.

Comparative Example 2

The content ratios of the chiral compound A, the chiral compound B, and the chiral compound C, and the handling properties of a commercially available TCDDM composition (2) (manufactured by Tokyo Chemical Industry Co., Ltd.) were evaluated. The evaluation results are shown in Table 1.

Comparative Example 3

The content ratios of the chiral compound A, the chiral compound B, and the chiral compound C, and the handling properties of a commercially available TCDDM composition (3) (manufactured by Merck) were evaluated. The evaluation results are shown in Table 1.

The TCDDM compositions obtained in Examples 1 to 3 and Comparative Examples 1 to 3 were subjected to the gas chromatography mass spectrometry by the method described above to measure the m/z and fragment patterns. It was confirmed that peaks 1 to 3 in each case showed the m/z and fragmentation patterns corresponding to TCDDM.

The representative fragments observed are as follows. MS(EI): 178 ([M-18]+), 165, 147, 119, 105, 91, 81, 67

TABLE 1

| | Component ratio of tricyclodecane dimethanol composition | | | | | Stringi- |
|---|---|---|---|---|---|---|
| | Xa/Xt | Xb/Xt | Xc/Xt | Xc/Xb | Xc/(Xa + Xb) | ness |
| Example 1 | 0.256 | 0.297 | 0.397 | 1.34 | 0.72 | A |
| Example 2 | 0.261 | 0.310 | 0.387 | 1.25 | 0.68 | B |
| Example 3 | 0.224 | 0.262 | 0.446 | 1.71 | 0.92 | A |
| Comparative Example 1 | 0.269 | 0.346 | 0.321 | 0.93 | 0.52 | C |
| Comparative Example 2 | 0.270 | 0.354 | 0.338 | 0.96 | 0.54 | C |
| Comparative Example 3 | 0.279 | 0.347 | 0.332 | 0.96 | 0.53 | C |

The TCDDM compositions obtained in Examples 1 to 3 had a high content of the chiral compound C and excellent crystallinity as a composition, so they were less likely to become stringy and had excellent handling properties.

The TCDDM compositions of Comparative Examples 1 to 3 had a low content of the chiral compound C and were more likely to become stringy and had poor handling properties.

Although the present invention has been described in detail with reference to particular embodiments, it will be apparent to those skilled in the art that various changes may be made thereto without departing from the spirit and scope of the present invention.

The present application is based on Japanese Patent Application No. 2022-042785 filed on Mar. 17, 2022, which is herein incorporated in its entirety by reference.

The invention claimed is:

1. A composition, comprising a tricyclodecane dimethanol mixture comprising:

a chiral compound A, one of whose enantiomers has formula (I);

a chiral compound B, one of whose enantiomers has formula (II);

a chiral compound C, one of whose enantiomers has formula (III), wherein a peak area Xa of the chiral compound A in the gas chromatogram, a peak area Xb of the chiral compound B in the gas chromatogram, and a peak area Xc of the chiral compound C in the gas chromatogram satisfy Xc/(Xa+Xb)≥0.60, and wherein the peak area Xc and a total peak areas Xt of all tricyclodecane dimethanols in the gas chromatogram satisfy Xc/Xt≥0.35

(I)

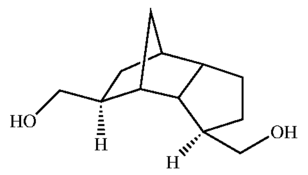

(II)

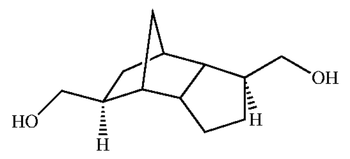

(III)

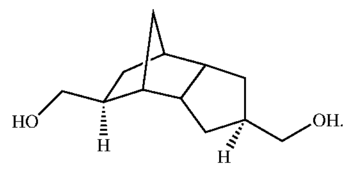

2. The composition of claim 1, wherein the peak area Xb and the peak area Xc satisfy Xc/Xb≥1.00.

3. The composition of claim 1, wherein the peak area Xa, the peak area Xb of, and the peak area Xc, satisfy $$1.10 \geqq Xc/(Xa+Xb) \geqq 0.60.$$

4. The composition of claim 1, wherein the peak area Xa and the total peak areas Xt satisfy Xa/Xt≤0.27.

5. The composition of claim 1, wherein the peak area Xb and the total peak areas Xt satisfy Xb/Xt≤0.32.

6. An ultraviolet curable composition, comprising: the composition of claim 1.

7. A hard coating material, comprising: the ultraviolet curable composition of claim 6.

8. A polymer composition, comprising: the ultraviolet curable composition of claim 6.

9. An antifouling coating material, comprising: the ultraviolet curable composition of claim 6.

10. A resist material, comprising: the ultraviolet curable composition of claim 6.

11. An inkjet ink, comprising: the ultraviolet curable composition of claim 6.

12. A material for a 3D printer, comprising: the ultraviolet curable composition of claim 6.

13. A polymer composition, comprising: the composition of claim 1.

14. The polymer composition of claim 13, wherein the polymer composition comprises a polyester resin, an epoxy resin, an acrylate resin, a polycarbonate resin, and/or a polyurethane resin.

15. A method for producing the composition of claim 1, the method comprising:

hydroformylating dicyclopentadiene to obtain tricyclodecane dicarbaldehydes;

obtaining a crude reaction solution containing tricyclodecane dimethanol by a reduction reaction of the tricyclodecane dicarbaldehydes; and distilling and purifying the crude reaction solution to obtain the composition.

16. The composition of claim 1, wherein the peak area Xc and the total peak areas Xt satisfy Xc/Xt≥0.38.

17. The composition of claim 1, wherein the peak area Xc and the total peak areas Xt satisfy $$0.55 \geqq Xc/Xt \geqq 0.35.$$

18. The composition of claim 1, wherein the peak area Xc and the total peak areas Xt satisfy $$0.50 \geqq Xc/Xt \geqq 0.38.$$

19. The composition of claim 1, wherein the peak area Xb and the peak area Xc satisfy $$2.0 \geqq Xc/Xb \geqq 1.25.$$

20. The composition of claim 1, wherein the peak area Xa, the peak area Xb, and the peak area Xc, satisfy $$1.00 \geqq Xc/(Xa+Xb) \geqq 0.70.$$

* * * * *